US006987172B2

(12) United States Patent
Boime et al.

(10) Patent No.: US 6,987,172 B2
(45) Date of Patent: Jan. 17, 2006

(54) MULTIFUNCTIONAL SINGLE CHAIN GLYCOPROTEIN HORMONES COMPRISING THREE OR MORE β SUBUNITS

(75) Inventors: Irving Boime, St. Louis, MO (US); Vicenta Garcia-Campayo, Chesterfield, MO (US)

(73) Assignee: Washington University in St. Louis, St. Louis, MO (US)

( * ) Notice: Subject to any disclaimer, the term of this patent is extended or adjusted under 35 U.S.C. 154(b) by 582 days.

(21) Appl. No.: 10/092,357

(22) Filed: Mar. 5, 2002

(65) Prior Publication Data

US 2002/0160944 A1    Oct. 31, 2002

Related U.S. Application Data

(60) Provisional application No. 60/273,521, filed on Mar. 5, 2001.

(51) Int. Cl.
C07K 14/59 (2006.01)
C07K 19/00 (2006.01)

(52) U.S. Cl. .............. 530/397; 530/398; 435/69.4; 435/69.7; 424/192.1; 424/198.1

(58) Field of Classification Search .............. None
See application file for complete search history.

(56) References Cited

U.S. PATENT DOCUMENTS

| | | | | |
|---|---|---|---|---|
| 5,705,478 | A * | 1/1998 | Boime | 514/8 |
| 5,958,737 | A * | 9/1999 | Boime et al. | 435/69.7 |
| 6,103,501 | A * | 8/2000 | Boime et al. | 435/69.7 |
| 6,225,449 | B1 * | 5/2001 | Boime | 530/399 |
| 6,242,580 | B1 * | 6/2001 | Boime et al. | 530/398 |
| 6,635,256 | B1 * | 10/2003 | Boime et al. | 424/192.1 |
| 6,689,365 | B1 * | 2/2004 | Boime | 424/192.1 |
| 6,693,074 | B1 | 2/2004 | Boime et al. | |

FOREIGN PATENT DOCUMENTS

| | | |
|---|---|---|
| WO | WO 90/09800 | 9/1990 |
| WO | WO 91/16922 | 11/1991 |
| WO | WO 94/24148 | 10/1994 |
| WO | WO 95/22340 | 8/1995 |
| WO | WO 96/05224 | 2/1996 |
| WO | WO 99/25849 | 5/1999 |
| WO | WO 00/23473 | 4/2000 |

OTHER PUBLICATIONS

Narayan et al. "A Biologically Active Single Chain Human Chorionic Gonadotropin Analog with Altered Receptor Binding Properties" Endocrinology 140:57-71 (1999).

* cited by examiner

*Primary Examiner*—Lorraine Spector
(74) *Attorney, Agent, or Firm*—Morrison & Foerster LLP

(57) ABSTRACT

Glycosylated or nonglycosylated molecules of the formula $$\beta^1\text{-(linker}^1)_{n^1}\text{-}\beta^2\text{-(linker}^2)_{n^2}\text{-}\beta^3\text{-(linker}^3)_{n^3}\text{-}\alpha; \quad (1)$$

$$\beta^1\text{-(linker}^1)_{n^1}\text{-}\beta^2\text{-(linker}^2)_{n^2}\text{-}\alpha\text{-(linker}^3)_{n^3}\text{-}\beta^3; \quad (2)$$

$$\beta^1\text{-(linker}^1)_{n^1}\text{-}\alpha\text{-(linker}^2)_{n^2}\text{-}\beta^2\text{-(linker}^3)_{n^3}\text{-}\beta^3; \quad (3)$$

and $$\alpha\text{-(linker}^1)_{n^1}\text{-}\beta^1\text{-(linker}^2)_{n^2}\text{-}\beta^2\text{-(linker}^3)_{n^3}\text{-}\beta^3 \quad (4)$$

wherein α is the α subunit of a vertebrate glycoprotein hormone or a variant thereof;
each β is independently a glycoprotein β subunit or a variant thereof,
each "linker" is a hydrophilic, flexible spacer equivalent to a peptide containing 1–100 amino acid residues; and each n is a 0 or 1;
said compound optionally comprising one or more additional $\beta^x$(linker$^x$)$_{n^x}$ and/or one or more additional α subunits are useful in protocols to enhance fertility in humans and in animals.

11 Claims, 4 Drawing Sheets

MULTIFUNCTIONAL SINGLE CHAIN GLYCOPROTEIN HORMONES COMPRISING THREE OR MORE β SUBUNITS

TECHNICAL FIELD

The invention relates to compositions that are useful in modulating fertility in humans and animals. More specifically, it concerns single chain forms of the glycoprotein hormones which contain multiple β subunits of the hormones luteinizing hormone (LH) follicle stimulating hormone (FSH), chorionic gonadotropin (CG), and/or thyroid stimulating hormone (TSH) coupled to one or more of the α subunit.

BACKGROUND ART

In humans, four important glycoprotein hormone heterodimers (LH, FSH, TSH and CG) have differing β subunits but identical α subunits. Three of these hormones are directly related to fertility, and the fourth, TSH, is indirectly so related. Three of these hormones, LH, FSH and TSH, are present in virtually all other vertebrate species; CG has so far been found only in primates and in the placenta and urine of pregnant mares.

PCT application WO 90/09800, published 7 Sep. 1990 and incorporated herein by reference, describes a number of modified forms of these hormones. One important modification is a C-terminal extension of the β subunit by the carboxy terminal peptide (CTP) of human chorionic gonadotropin or a variant thereof. CTP is the sequence of amino acids extending from any one of positions 112–118 to position 145 of the β subunit of human chorionic gonadotropin. PCT publication WO 94/24148 published 27 Oct. 1994 and incorporated herein by reference describes modifying these hormones by addition of the CTP at locations other than the C-terminus as well as variants of the CTP itself which are shorter than the sequence defined above.

PCT publication WO 91/16922 published 14 Nov. 1991 describes a number of chimeric and otherwise modified forms of the heterodimeric glycoprotein hormones. This disclosure is incorporated herein by reference as well. In addition, two PCT publications describe single chain forms of these hormones wherein the α and β subunits are covalently linked to result in a fusion peptide of the formula β(linker)$_n$α, or α(linker)$_n$β, wherein n is 0 or 1 and α and β represent the respective subunits of these hormones. These publications, WO 95/22340 published 24 Aug. 1995 and WO 96/05224 published 22 Feb. 1996 are incorporated herein by reference.

Forms of the single chain glycoprotein hormones in which the number of cystine bridges has been depleted are disclosed in U.S. Pat. No. 6,693,074 filed 19 Sep. 1997 and incorporated herein by reference.

PCT publication WO 99/25849 published 27 May 1999 and incorporated herein by reference describes covalent single chain forms of the glycoprotein hormones which contain two β subunits. The two β subunits may be the same or different and may be coupled through linkers to each other and to a common α subunit. These compounds are of the formulas β$^1$-(linker$^1$)$_m$-α-(linker$^2$)$_n$-β$^2$;

β$^1$-(linker$^1$)$_m$-β$^2$-(linker$^2$)$_n$-α; and

α-(linker$^1$)$_m$-β$^1$-(linker$^2$)$_n$-β$^2$.

the two β subunits are different, the single chain forms are multifunctional.

In addition, PCT publication WO 00/23473 published 27 Apr. 2000 and incorporated herein by reference also describes modified forms of these single chain hormones wherein one of the β subunits is coupled covalently, optionally through a linker to the α subunit while a second β subunit is non-covalently associated with the single chain form.

U.S. Pat. No. 6,689,365 filed 5 May 2000 and incorporated herein by reference describes a subgenus of single chain forms of the formula

FSHβ-(linker$^1$)$_{n1}$-LHβ(1−x)-(linker$^2$)$_{n2}$-α wherein LHβ(1−x) refers to the LHβ subunit optionally containing deletions of up to 7 amino acids from the carboxy terminus and each linker is an amino acid sequence which is flexible and hydrophilic; each n is 0 or 1. By adjusting the lengths of the linkers, especially that between the LHβ subunit and α, the ratio of FSH to LH activity can be fine-tuned.

Thus, while the art describes single chain multifunctional glycoprotein hormone forms, the multifunctionality has been limited to that ascribable to only two of the glycoprotein hormone heterodimers. It has now been found that single chain forms can be constructed wherein the activity of at least three of the hormones can be exhibited based on a single molecule. The relative degrees of these activities can be adjusted by controlling the spacing within the construct.

DISCLOSURE OF THE INVENTION

The compounds of the invention contain three or more β subunits, which may be the same or different, coupled to one or more α subunits optionally through linking moieties of variable lengths. Thus, the compounds of the invention are of the formulas:

$$\beta^1\text{-(linker}^1)_{n1}\text{-}\beta^2\text{-(linker}^2)_{n2}\text{-}\beta^3\text{-(linker}^3)_{n3}\text{-}\alpha \quad (1);$$

$$\beta^1\text{-(linker}^1)_{n1}\text{-}\beta^2\text{-(linker}^2)n2\text{-}\alpha\text{-(linker}^3)_{n3}\text{-}\beta^3 \quad (2);$$

$$\beta^1\text{-(linker}^1)_{n1}\text{-}\alpha\text{-(linker}^2)_{n2}\text{-}\beta^2\text{-(linker}^3)_{n3}\text{-}\beta^3 \quad (3);$$

and $$\alpha\text{-(linker}^1)_{n1}\text{-}\beta^1\text{-}\beta^1\text{-(linker}^2)_{n2}\text{-}\beta^2\text{-(linker}^3)_{n3}\text{-}\beta^3 \quad (4)$$

wherein α designates the α subunit common to the glycoprotein hormones or a variant thereof, each β is independently the β subunit of one of said glycoprotein hormones or a variant thereof and each linker is independently a flexible hydrophilic moiety that distances the coupled subunits by a spacing equivalent to that generated by 1–100 amino acids, preferably 1–50 amino acids and each n is independently 0 or 1. In addition, the above formulas may include one or two additional α subunits along with an optional linker in positions which do not link the α subunit to the α subunit already present, and may also contain one or more additional β subunits linked at any position. The α and β subunits or variants may be based on the human forms or the forms derived from other vertebrates, such as other primates, and preferably mammalian forms. The level of activity of the various β subunits can be adjusted by adjusting linker length.

Thus, in one aspect, the invention is directed to compounds of formulas (1)–(4); in other aspects, the invention is directed to recombinant materials for the production of these compounds and to methods for their production as well as to methods for their use. In still other aspects, the invention is directed to antibodies which are specifically immunoreactive with the compounds of the invention and to formulations suitable for pharmaceutical and veterinary use containing these compounds or the corresponding recombinant materials.

MODES OF CARRYING OUT THE INVENTION

Figure 1:
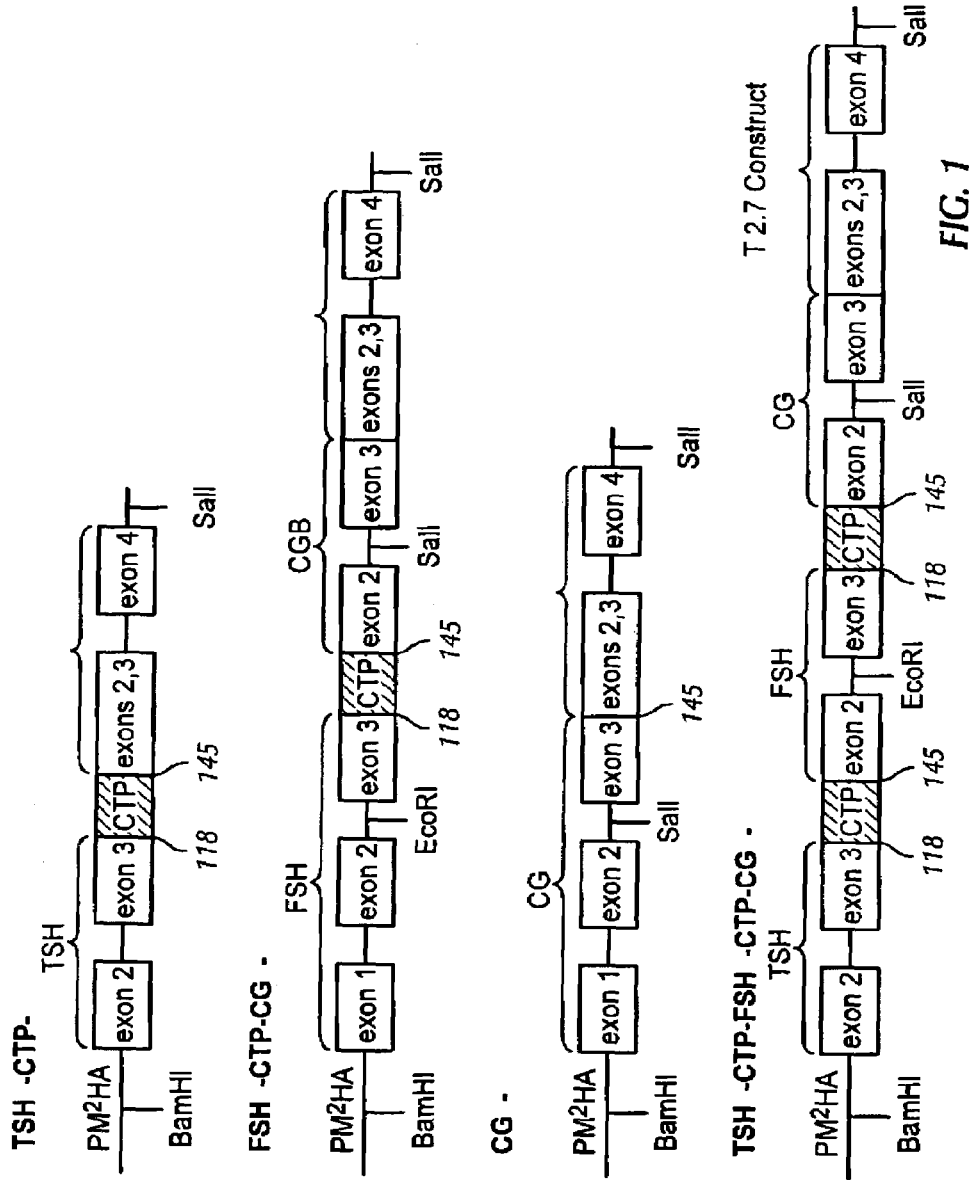
FIG. 1 is a schematic of a construct for the production of TSHβ-CTP-FSHβ-CTP-CGβ-α.

Four "glycoprotein" hormones in humans provide a family which includes human chorionic gonadotropin (hCG), follicle stimulating hormone (FSH), luteinizing hormone (LH), and thyroid stimulating hormone (TSH). All of these hormones are heterodimers comprised of α subunits which, for a given species, are identical in amino acid sequence among the group, and β subunits which differ according to each member of the family. Thus, normally these glycoprotein hormones occur as heterodimers composed of α and β subunits that are non-covalently associated. Most vertebrates produce FSH, TSH and LH; chorionic gonadotropin has been found only in primates, including humans, and in pregnant mares.

In animals, the α and β subunit of each hormone are encoded by different genes and are synthesized separately and then assembled into the noncovalent heterodimeric complex. In the compounds of the invention at least three β subunits are covalently linked to at least one α subunit to form a single-chain molecule which is essentially linear in primary structure. The three dimensional structure conferred by secondary and tertiary structural considerations and energy of conformation is apparently sufficiently similar to the heterodimeric form to permit the functionality of the heterodimer represented by each of the β subunits to be exhibited. The compounds of the present invention are particularly advantageous in the design of pharmaceuticals for inducing or controlling fertility since a multiplicity of hormone functions can be introduced. Although LH, hCG and FSH are directly involved in the physiological functions which control fertility, and thus are of apparent use in this regard, it should be noted that TSH is an important element in such compositions since deficiencies in thyroid production affect ovulation.

The correlation between TSH and reproductive issues is well established. This has been reviewed, for example, in Mayer, et al., *Thyroid and Fertility* (1998) 22:17–21. The correlation between thyroid conditions and female reproductive conditions is discussed by Krassas, G. E., et al., *Fertil. Steril.* (2000) 74:2063–2070. The correlation in adult male rats is discussed by Jiang, J. Y., et al., *Biol Repro.* (2000) 63:1637–1641. Further discussions of the correlation between thyroid function and human reproduction are found in articles by Vierhapper, H., *Hum. Repro.* (1997) 12:2856; Moncayo, H. E., et al., ibid. 2854–2856.

In treating cells either in in vitro or in vivo for induction of fertility, it is desirable to provide the effects of follicle stimulating hormone (FSH) as the major component. However, it is advantageous to provide a typically lesser, but nevertheless significant amount of activity with respect for receptors for chorionic gonadotropin/luteinizing hormone. (The same receptor recognizes both CG and LH). The degree of LH activity that is desirable varies somewhat with the particular subject or cells to be treated, but it is typically substantially less than that of the FSH activity. TSH activity may also be required when the treatment is in vivo. By suitable manipulations of the components of the compounds of the invention, including the nature and length of the various optional linkers, the activity of the compound with respect to interaction with receptors for the various hormones can be well controlled.

Thus, by adjusting the precise nature of the various components of the single chain compounds of the invention, the strength of the dosage and the duration of the dosage of each individual component can be varied relative to the remaining components while providing the opportunity to administer all of these activities as a single dose. Such single dosage forms have considerable advantages in the practical application of fertility or infertility treatments. For example, the dosage strength of FSH could be increased by providing more than a single β subunit of FSH or by adjusting the spacing of the FSH from other components of the compound. The duration of the dosage can be altered by altering the glycosylation state of the β subunits, each individually such that a finely tuned time course of administration of each component can be achieved by administration of a single compound.

The Subunit Components

As used herein, the common α subunit, and FSHβ, LHβ, and CGβ subunits as well as the heterodimeric forms have their conventional definitions and refer to the proteins having the amino acid sequences known in the art per se, or allelic variants thereof, regardless of the glycosylation pattern exhibited or other derivatization of the amino acid side chains.

"Native" forms of these peptides are those which have the amino acid sequences that have been isolated from the relevant vertebrate tissue, and have these known sequences per se, or those of their allelic variants.

"Variant" forms of the subunits in the proteins and of CTP units (see below) are those which have deliberate alterations, including truncations, in amino acid sequences of the native protein produced by, for example, site-specific mutagenesis or by other recombinant manipulations, or which are prepared synthetically.

These alterations consist of 1–7, preferably 1–5, more preferably 1–3, and even more preferably 1 amino acid changes, including deletions, and/or insertions, and/or substitutions, including in addition to non-conservative substitutions, conservative amino acid substitutions. The resulting variants must retain an activity that reflects that the native hormone—i.e., they must retain the biological activity of the native hormone so as to behave as agonists.

"Conservative analog" means, in the conventional sense, an analog wherein the residue substituted is of the same general amino acid category as that for which substitution is made. Amino acids have been classified into such groups, as is understood in the art, by, for example, Dayhoff, M., et al., *Atlas of Protein Sequences and Structure* (1972) 5:89–99. In general, acidic amino acids fall into one group; basic amino acids into another; neutral hydrophilic amino acids into another; and so forth. More specific classifications are set forth in WO 96/05224 incorporated by reference above.

One set of preferred variants is that wherein the glycosylation sites of either the α or β subunits or both or of the CTP or partial CTP have been altered. Some useful variants of the hormone quartet described herein are set forth in U.S. Pat. No. 5,177,193 issued 5 Jan. 1993 and incorporated herein by reference. The glycosylation patterns can be altered by destroying the relevant sites, by adding one or more sites, or, in the alternative, by changing the host cell in which the protein is produced.

Variants also include those with noncritical regions altered or removed. Such deletions and alterations may comprise entire loops, so that sequences of considerably more than 10 amino acids may be deleted or changed. The resulting variants must, however, retain at least the receptor binding domains and the regions involved in signal transduction.

There is considerable literature on variants of the glycoprotein hormones and it is clear that a large number of possible variants which result in agonist activity can be prepared. Such variants are disclosed, for example, in Chen, F., et al., *Molec Endocrinol* (1992) 6:914–919; Yoo, J., et al., *J Biol Chem* (1993) 268:13034–13042; Yoo, J., et al., *J Biol Chem* (1991) 266:17741–17743; Puett, D., et al., *Glycoprotein Hormones*, Lusbader, J. W., et al., EDS, *Springer Verlag* New York (1994) 122–134; Kuetmann, H. T., et al., (ibid.) pages 103–117; Erickson, L. D., et al., *Endocrinology* (1990) 126:2555–2560; and Bielinska, M., et al., *J Cell Biol* (1990) 111:330a (Abstract 1844).

Other variants include those wherein one or more cystine-bonds are deleted, typically by substituting a neutral amino acid for one or both cysteines which participate in the link. Particularly preferred cystine bonds which may be deleted are those between positions 26 and 110 and between positions 23 and 72 in the human forms and corresponding positions in other vertebrate forms.

As used herein "peptide" and "protein" are used interchangeably, since the length distinction between them is arbitrary.

"Noncritical" regions of the α and β subunits are those regions of the molecules not required for biological activity. In general, these regions are distant from binding sites, precursor cleavage sites, and catalytic regions. Regions critical for inducing proper folding, binding to receptors, catalytic activity and the like should be evaluated. It should be noted that some of the regions which are critical in the case of the dimer become noncritical in single chain forms since the conformational restriction imposed by the molecule may obviate the necessity for these regions. The ascertainment of noncritical regions is readily accomplished by deleting or modifying candidate regions and conducting an appropriate assay for the desired activity. Regions where modifications result in loss of activity are critical; regions wherein the alteration results in the same or similar activity are considered noncritical.

As used herein, the "CTP unit" refers to an amino acid sequence found at the carboxy terminus of human chorionic gonadotropin β subunit which extends from amino acid 112–118 to residue 145 at the C-terminus. Thus, each "complete" CTP unit contains 28–34 amino acids, depending on the N-terminus of the CTP.

By a "partial" CTP unit is meant an amino acid sequence which occurs between positions 112–118 to 145 inclusive, but which has at least one amino acid deleted from the shortest possible "complete" CTP unit (i.e., from positions 118–145). These "partial" sequences are included in the definition of "variants" with respect to CTP. The "partial" CTP units contain at least one O-glycosylation site. The CTP unit contains four glycosylation sites at the serine residues at positions 121 (site 1); 127 (site 2); 132 (site 3); and 138 (site 4). The partial forms of CTP useful in agonists will contain one or more of these sites arranged in the order in which they appear in the native CTP sequence, although intervening sites may be omitted.

Preferred Compounds

In the compounds of formulas (1)–(4), each β subunit may be different, or all β subunits may be the same, or two may be the same and the other different. Because CG and LH are recognized by the same receptor, in many embodiments, the β subunits of these hormones are interchangeable. As CGβ automatically contains a CTP, when CGβ resides in the molecule, it is preferred that it be coupled to the downstream portion with a shorter linker or no linker at all as compared to the remaining β subunits. Preferred embodiments of the linkers in general include CTP units and variants thereof as defined above.

While the invention is illustrated by a tetramer which contains, in addition to the common α subunit, β subunits from all three types of activities: FSH, TSH and CG/LH, additional α and β subunits can also be employed. In a particularly preferred embodiment, all four β subunits, CGβ, LHβ, FSHβ and TSHβ are included. In this family, in embodiments where only one α subunit is present, the compounds are of the form $$\beta^1(\text{linker}^1)_{n^1}\text{-}\beta^2(\text{linker}^2)_{n^2}\text{-}\beta^3(\text{linker}^3)_{n^3}\text{-}\beta^4(\text{linker}^4)_{n^4}\text{-}\alpha, \quad (5)$$

$$\beta^1(\text{linker}^1)_{n^1}\text{-}\beta^2(\text{linker}^2)_{n^2}\text{-}\beta^3(\text{linker}^3)_{n^3}\text{-}\alpha\text{-}\beta^4(\text{linker}^4)_{n^4}, \quad (6)$$

$$\beta^1(\text{linker}^1)_{n^1}\text{-}\beta^2(\text{linker}^2)_{n^2}\text{-}\alpha\text{-}\beta^3(\text{linker}^3)_{n^3}\text{-}\beta^4(\text{linker}^4)_{n^4}, \quad (7)$$

$$\beta^1(\text{linker}^1)_{n^1}\text{-}\alpha\text{-}\beta^2(\text{linker}^2)_{n^2}\text{-}\beta^3(\text{linker}^3)_{n^3}\text{-}\beta^4(\text{linker}^4)_{n^4}, \quad (8)$$

$$\alpha\text{-}\beta^1(\text{linker}^1)_{n^1}\text{-}\beta^2(\text{linker}^2)_{n^2}\text{-}\beta^3(\text{linker}^3)_{n^3}\text{-}\beta^4(\text{linker}^4)_{n^4}. \quad (9)$$

Particularly preferred, among these, are embodiments wherein each of the β subunits is of a different hormone—i.e., in any order, βCG, βLH, βTSH and βFSH.

In general, the linker moieties space the components of the molecules derived from the glycoprotein hormones at distances equivalent to 1–100 amino acids, preferably 1–50 amino acids. It is most preferred that the linkers consist of a peptide of 1–50 gene-encoded amino acids so that recombinant production of the compounds of formulas (1)–(4) is practical. The linkers may preferably comprise, as stated above, CTP units or partial CTP units, but may also consist of sequences of hydrophilic amino acids or amino acids lacking substantial side chains, such as glycine and serine. In general, the linkers should be hydrophilic.

However, as it is possible to produce the compounds of formulas (1)–(4) synthetically, the linkers need not necessarily consist of naturally occurring amino acids but may include non-naturally occurring counterparts, and may also include hydrophilic linkers in general, such as polyethylene glycols or substituted polyesters or polyamides. The subunits derived from the glycoprotein hormones are preferably linked in a head-tail sequence, again permitting recombinant production of these peptides, but may also be linked headhead (i.e., through the N-termini, in this case requiring a linker) or tail-tail (again requiring a linker).

By adjusting the nature of the linkers, the glycosylation levels of the single chain multifunctional hormone can be adjusted. One advantage of the multiplicity of β subunits is also an inherently higher level of glycosylation, which is believed to enhance half-life. Thus, the compounds of the invention have the inherent advantage of long half-life.

Particularly preferred embodiments of the hormones of the invention include, shown N-C:

TSHβ-FSHβ-CTP-LHβ(1–114)-α;

CGβ-LHβ-CTP-FSHβ-α;

FSHβ-CTP-LHβ-TSHβ-α;

FSHβ-LHβ-CGβ-α;

TSHβ-CTP-FSHβ-CTP-CGβ-LHβ-CTP-α;

TSHβ-α-LHβ-CTP-FSHβ;

FSHβ-CTP-LHβ-CTP-CG-α;

FSHβ-α-LHβ-CTP-CGβ;

FSHβ-LHβ-α-CGβ-TSHβ;

LHβ-CTP-TSHβ-CTP-α-CGβ;

CGβ-FSHβ-CTP-LHβ-α-TSHβ-CTP;

TSHβ-FSHβ-CTP-α-LHβ-CTP.

In all of the above, the CTP linkers maybe complete—i.e., 112–145, 113–145 . . . 118–145, or partial.

While for human use, the human forms of the α and β subunits are desirable, it should be noted that the corresponding forms in other vertebrates are useful in veterinary contexts. The FSH, TSH and LH subunits from bovine, ovine, equine, porcine, feline, canine, and other species are appropriate to indications affecting these species.

Other Modifications

The single-chain proteins of the invention may be further conjugated or derivatized in ways generally understood to modify amino acid sequences, such as phosphorylation, glycosylation (both N- and O- linked), deglycosylation of ordinarily glycosylated forms, acylation, modification of amino acid side chains (e.g., conversion of proline to hydroxyproline) and similar modifications analogous to those posttranslational events which have been found to occur generally.

The glycosylation status of the hormones of the invention is particularly important. The hormones may be prepared in nonglycosylated form either by producing them in prokaryotic hosts or by mutating the glycosylation sites normally present in the subunits and/or any CTP units that may be present. Both nonglycosylated versions and partially glycosylated versions of the hormones can be prepared by manipulating the glycosylation sites. Normally, glycosylated versions are, of course, also included within the scope of the invention.

As is generally known in the art, the single-chain proteins of the invention may also be coupled to labels, carriers, solid supports, and the like, depending on the desired application. The labeled forms may be used to track their metabolic fate; suitable labels for this purpose include, especially, radioisotope labels such as iodine 131, technetium 99, indium 111, and the like. The labels may also be used to mediate detection of the single-chain proteins in assay systems; in this instance, radioisotopes may also be used as well as enzyme labels, fluorescent labels, chromogenic labels, and the like. The use of such labels permits localization of the relevant receptors since they can be used as targeting agents for such receptors.

The proteins of the invention may also be coupled to carriers to enhance their immunogenicity in the preparation of antibodies specifically immunoreactive with these new modified forms. Suitable carriers for this purpose include keyhole limpet hemocyanin (KLH), bovine serum albumin (BSA) and diphtheria toxoid, and the like. Standard coupling techniques for linking the modified peptides of the invention to carriers, including the use of biofunctional linkers, can be employed.

Similar linking techniques, along with others, may be employed to couple the proteins of the invention to solid supports. When coupled, these proteins can then be used as affinity reagents for the separation of desired components with which specific reaction is exhibited. Thus, they are useful in the purification and isolation of the receptors with which the appropriate β subunit interacts.

Preparation Methods

Methods to construct the proteins of the invention are well known in the art. The most practical approach at present is to synthesize these materials recombinantly by expression of the nucleotide sequence encoding the desired protein. A nucleic acid containing the nucleotide sequence encoding the single-chain forms, including variants, can be prepared from native sequences, or synthesized de novo or using combinations of these techniques. Techniques for site-directed mutagenesis, ligation of additional sequences, amplification such as by PCR, and construction of suitable expression systems are all, by now, well known in the art. Portions or all of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available compatible with a wide variety of hosts, including prokaryotic hosts such as *E. coli* or *B. subtilis* and eucaryotic hosts such as yeast, other fungi such as *Aspergillus* and *Neurospora*, plant cells, insect cells, mammalian cells such as CHO cells, avian cells, and the like.

The choice of host is particularly pertinent to posttranslational events, most particularly including glycosylation. The location of glycosylation is mostly controlled by the nature of the glycosylation sites within the molecule; however, the nature of the sugars occupying this site is also influenced by the nature of the host. Accordingly, a fine-tuning of the properties of the hormones of the invention can be achieved by proper choice of host.

A particularly preferred form of gene for the α subunit portion, whether the α subunit is modified or unmodified, is the "minigene" construction. As used herein, the α subunit "minigene" refers to the gene construction disclosed in Matzuk, M. M., et al., *Mol Endocrinol* (1988) 2:95–100, in the description of the construction of $pM^2/CG$ α or $pM^2/α$.

For recombinant production, modified host cells using expression systems are used and cultured to produce the desired protein. These terms are used herein as follows:

A "modified" recombinant host cell, i.e., a cell "modified to contain" the recombinant expression systems of the invention, refers to a host cell which has been altered to contain this expression system by any convenient manner of introducing it, including transfection, viral infection, and so forth. "Modified cells" refers to cells containing this expression system whether the system is integrated into the chromosome or is extrachromosomal. The "modified cells" may either be stable with respect to inclusion of the expression system or the encoding sequence may be transiently expressed. In short, recombinant host cells "modified" with the expression system of the invention refers to cells which include this expression system as a result of their manipulation to include it, when they natively do not, regardless of the manner of effecting this incorporation.

"Expression system" refers to a nucleic acid molecule which includes a coding nucleotide sequence to be expressed and those accompanying control sequences necessary to effect the expression of the coding sequence. Typically, these controls include a promoter, termination regulating sequences, and, in some cases, an operator or other mechanism to regulate expression. The control sequences are those which are designed to be functional in a particular target recombinant host cell and therefore the host cell must be chosen so as to be compatible with the control sequences in the constructed expression system.

If secretion of the protein produced is desired, an additional nucleotide sequence encoding a signal peptide is also included so as to produce the signal peptide operably linked to the desired single-chain hormone to produce the preprotein. During translation, the signal peptide is cleaved to release the mature single-chain hormone.

As used herein "cells," "cell cultures," and "cell lines" are used interchangeably without particular attention to nuances of meaning. Where the distinction between them is important, it will be clear from the context. Where any can be meant, all are intended to be included.

The protein produced may be recovered from the lysate of the cells if produced intracellularly, or from the medium if secreted. Techniques for recovering recombinant proteins from cell cultures are well understood in the art, and these proteins can be purified using known techniques such as chromatography, gel electrophoresis, selective precipitation, and the like.

All or a portion of the hormones of the invention may be synthesized directly using peptide synthesis techniques known in the art and synthesized portions may be ligated chemically or enzymatically.

Antibodies

The proteins of the invention may be used to generate antibodies specifically immunoreactive with these new compounds. These antibodies are useful in a variety of diagnostic and therapeutic applications.

The antibodies are generally prepared using standard immunization protocols in mammals such as rabbits, mice, sheep or rats, and the antibodies are titered as polyclonal antisera to assure adequate immunization. The polyclonal antisera can then be harvested as such for use in, for example, immunoassays. Antibody-secreting cells from the host, such as spleen cells, or peripheral blood leukocytes, may be immortalized using known techniques and screened for production of monoclonal antibodies immunospecific with the proteins of the invention. "Antibodies" include any fragment which retains the required immunospecificity, such as $F_{ab}$, $F_{ab'}$, $F_{(ab')2}$, $F_v$ and so forth. Thus, the antibodies may also be prepared using recombinant techniques, typically by isolating nucleotide sequences encoding at least the variable regions of monoclonal antibodies with the appropriate specificity and constructing appropriate expression systems. This approach permits any desired modification such as production of $F_v$ forms, chimeric forms, "humanized" forms and the like.

By "immunospecific for the proteins of the invention" is meant antibodies which specifically bind the referent compound of the invention, but not the heterodimers or any of the included subunits per se or any single-chain forms which include only a single or only two β subunits, within the general parameters considered to determine affinity or non-affinity. It is understood that specificity is a relative term, and an arbitrary limit could be chosen, such as a difference in specific binding of 100-fold or greater. Thus, an immunospecific antibody included within the invention is at least 100 times more reactive with the specified protein than with the corresponding heterodimers, prior art single-chain forms or separate subunits. Such antibodies can be obtained, for example, by screening for those that bind the invention compounds and discarding those that also bind the heterodimers, subunits or prior art single-chain forms.

The antibodies of the invention are particularly useful in assessing the levels of the invention compounds in the body fluids of a subject. Thus, therapeutic protocols can be monitored conveniently using standard immunoassays involving these antibodies or fragments as defined above. In addition, the antibodies are useful in purification of the single chain compounds of the invention and in analysis for production of these proteins in various contexts, including synthetic and recombinant systems.

Formulation and Methods of Use

The proteins of the invention are formulated and administered using methods comparable to those known for the heterodimers corresponding to them. Thus, formulation and administration methods will vary according to the particular hormone or hormone combination used. However, the dosage level and frequency of administration may be altered as compared to the heterodimer, especially if CTP units are present in view of the extended biological half life due to its presence.

Formulations for proteins of the invention are those typical of protein or peptide drugs such as found in *Remington's Pharmaceutical Sciences,* latest edition, Mack Publishing Company, Easton, Pa. Generally, proteins are administered by injection, typically intravenous, intramuscular, subcutaneous, or intraperitoneal injection, or using formulations for transmucosal or transdermal delivery. These formulations generally include a detergent or penetrant such as bile salts, fusidic acids, and the like. These formulations can be administered as aerosols or suppositories or, in the case of transdermal administration, in the form of skin patches. Oral administration is also possible provided the formulation protects the peptides of the invention from degradation in the digestive system.

Optimization of dosage regimen and formulation is conducted as a routine matter and as generally performed in the art. These formulations can also be modified to include those suitable for veterinary use.

The compounds of the invention may be used in many ways, most evidently as substitutes for the heterodimeric forms of the hormones. Thus, like the heterodimers, the agonist forms of the single-chain hormones of the invention can be used in treatment of infertility, as aids in in vitro fertilization techniques, and other therapeutic methods associated with the native hormones. These techniques are applicable to humans as well as to other animals. The choice of the single-chain protein in terms of its species derivation will, of course, depend on the subject to which the method is applied.

The invention compounds are also useful as reagents in a manner similar to that employed with respect to the heterodimers.

In addition, the compounds of the invention may be used as diagnostic tools to detect the presence or absence of antibodies that bind to the native proteins to the extent such antibodies bind to the relevant portions of these single chain compounds in biological samples. They are also useful as control reagents in assay kits for assessing the levels of these hormones in various samples. Protocols for assessing levels of the hormones themselves or of antibodies raised against them are standard immunoassay protocols commonly known in the art. Various competitive and direct assay methods can be used involving a variety of labeling techniques including radio-isotope labeling, fluorescence labeling, enzyme labeling and the like.

The compounds of the invention are also useful in detecting and purifying receptors to which the native hormones bind. Thus, the compounds of the invention may be coupled to solid supports and used in affinity chromatographic preparation of receptors or antihormone antibodies. The resulting receptors are themselves useful in assessing hormone activity for candidate drugs in screening tests for therapeutic and reagent candidates. Of course, account must be taken of the specificity of the β subunits if the β subunits are different.

Finally, the antibodies uniquely reactive with the compounds of the invention can be used as purification tools for isolation of these materials in their subsequent preparations. They can also be used to monitor levels of these compounds administered as drugs.

The following examples are intended to illustrate but not to limit the invention.

EXAMPLE 1

Preparation of Invention Compounds

Expression vectors were prepared for production of the proteins and their secretion from Chinese hamster ovary (CHO) cells. The construct of the nucleotide sequence encoding the compound that was prepared and tested is shown in FIG. 1. This compound is TSHβ-CTP-FSHβ-CTP-CGβ-α.

In this construct, the various β subunits and α subunit are the human forms. The expression system is constructed in a derivative of $pM^2$ a vector originally described in Matzuk, M. M., et al., *Mol Endocrinol* (1988) 2:95–100. The derivative vector, $pM^2HA$, contains a polylinker which includes a number of unique cloning sites as described by Sachais, B., et al., *J Biol. Chem.* (1993) 268:2319–2323. This vector, containing a single chain construct comprising CGβ-α as shown in FIG. 1 is described in Sugihara, T., et al., *Proc. Natl. Acad. Sci. USA* (1995) 92:2041–2045. As shown in FIG. 1, the three exons of the CGβ coding sequence from positions 1–145 are directly fused to the exons which constitute the α subunit encoding sequence. The upstream FSHβ-CTP portion of the final construct to prepare the construct containing exons 1, 2 and 3 of the FSHβ encoding sequence which is fused to the nucleotide sequence encoding positions 118–145 of CGβ as described by Kanda, M., et al., *Mol. Endocrinol.* (1999) 13:1873–1881 and as shown in FIG. 1. The upstream TSHβ portion is then obtained from the construct described by Fares, F., et al., *Endocrinol.* (1998) 139:2459–2464 to obtain the final construct depicted in FIG. 1.

The resulting vector was transfected into CHO cells and the cells were cultured to encourage expression. The tetramer, designated T2-7, containing the three β subunits and α subunit was secreted successfully and its identity confirmed on Western blot using monoclonal antibodies directed to FSHβ, CGβ and TSHβ and by antibodies to human α. All of these antibodies bind to a secreted protein of the proper size.

EXAMPLE 2

Binding of the LH or FSH Receptor

The tetramer compound of Example 1 was tested for its ability to compete for binding to receptor with I-125 labeled hCG or FSH heterodimers or other constructs as appropriate. The procedures for assay are those set forth in Kanda, M., et al., *Mol Endocrinol* (1999) 13:1873–1881, cited above and incorporated herein by reference.

Figure 2:
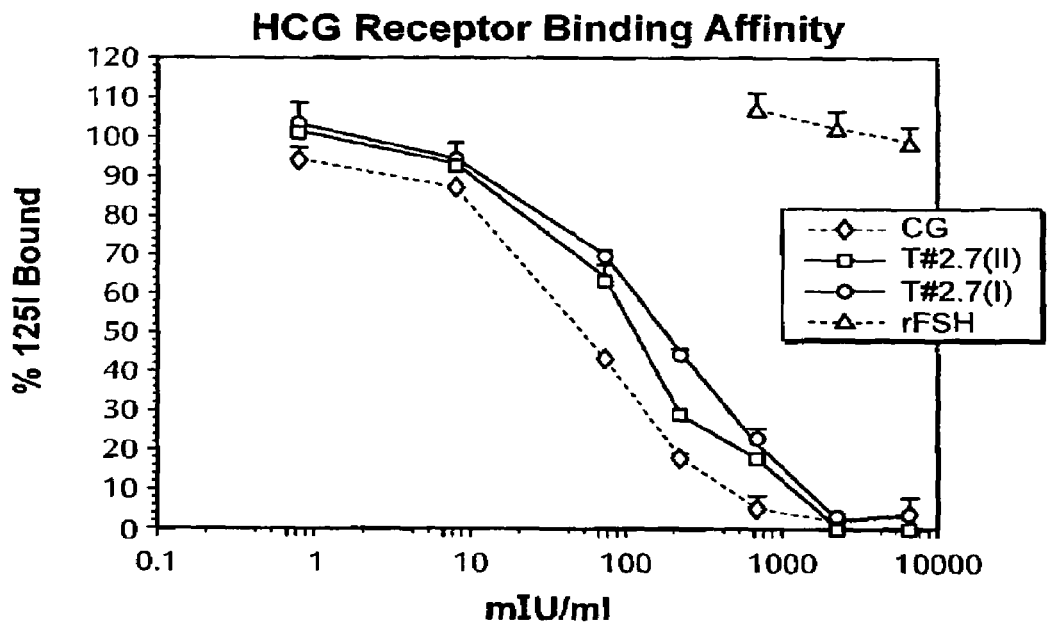
FIG. 2 is a graph showing the ability of the product of the construct shown in FIG. 1 to bind the human chorionic gonadotropin (hCG) receptor in competition with labeled recombinant hCG.

Briefly, for assessing binding to the CG/LH receptor, CHO cells expressing human LH receptor ($4 \times 10^5$/tube) were incubated with one ng labeled CG in competition with increasing concentrations of unlabeled CG as a standard or with increasing amounts of the samples to be tested, at 22° C. for 18 hours. The decrease in label in the presence of sample measures the binding ability in the sample. The results are shown in FIG. 2.

As shown, both T2.7 constructs show binding affinity comparable to that of the CG heterodimer (solid diamonds). The tetramer construct (solid squares) provides an $EC_{50}$ only approximately 5 fold more than the CG heterodimer. Several repetitions of this assay, however, show that the tetramer binds to the CG receptor with an $EC_{50}$ of only two-three fold higher than the heterodimer.

Figure 3:
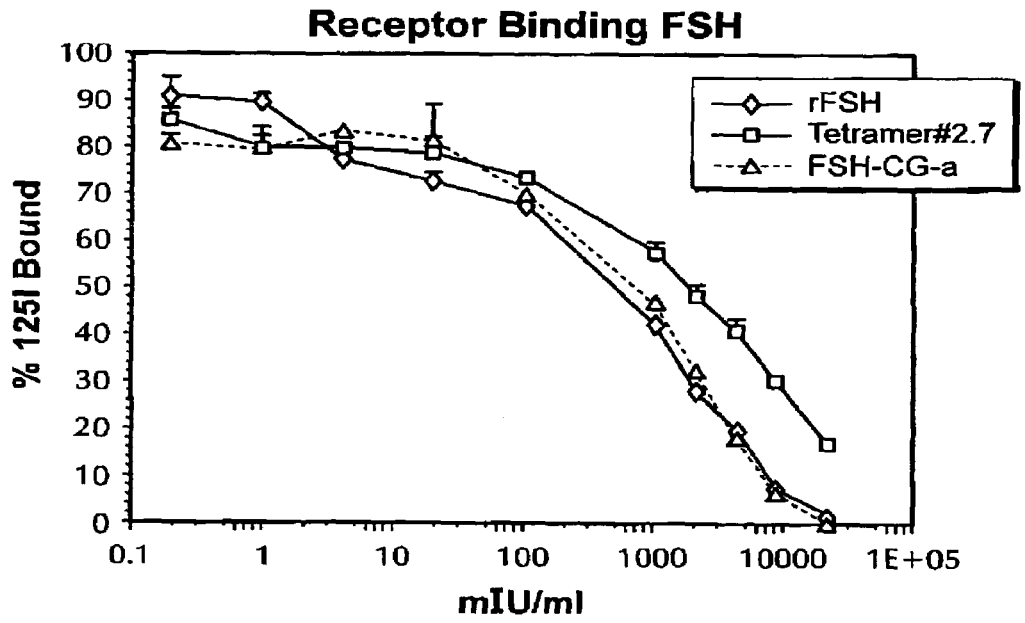
FIG. 3 is a graph showing the ability of the construct shown in FIG. 1 to bind FSH receptor.

A comparable essay testing ability of the compounds to bind the FSH receptor displayed on CHO cells in competition with I-125 labeled FSH, in a protocol otherwise identical to that set forth above, was also performed. These results are shown in FIG. 3. Again, the tetramer to the FSH receptor shows only slightly less affinity to receptor than the recombinantly produced heterodimer or the single chain trimer, FSH-CG-α.

EXAMPLE 3

Agonist Activity With Respect to LH, FSH and TSH

The tetramer of Example 1 was tested for ability to stimulate cyclic AMP production in CHO cells that display the CG/LH receptor, the FSH receptor, or the TSH receptor. The procedure is that of Kanda, et al., (1999) cited above. Briefly, the total extracellular and intracellular amount of cAMP is determined using the Adenyl Cyclase Activation Flash Plate Kit (NEN Life Science Products, Boston Mass.) as per the manufacturer's instructions. CHO cells ($5 \times 10^4$ cells per well) expressing either LH/CG, FSH or TSH receptor were incubated with tetramer or control for 2 hours at room temperature. cAMP labeled with I-125 was added and the cells were incubated for an additional 16–18 hours at room temperature. The flash plates were read in a Packard Top gamma counter and each experiment was performed 2–3 times. The cAMP content is expressed in pmol/ml.

Figure 4:
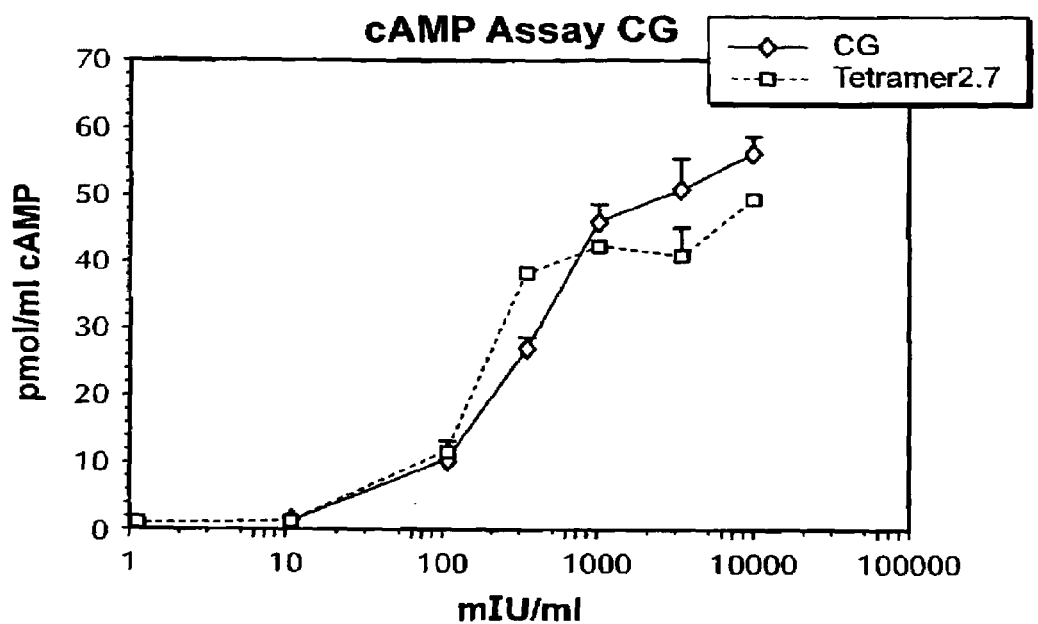
FIG. 4 is a graph showing the ability of the construct of FIG. 1 to activate the CG receptor.
Figure 5:
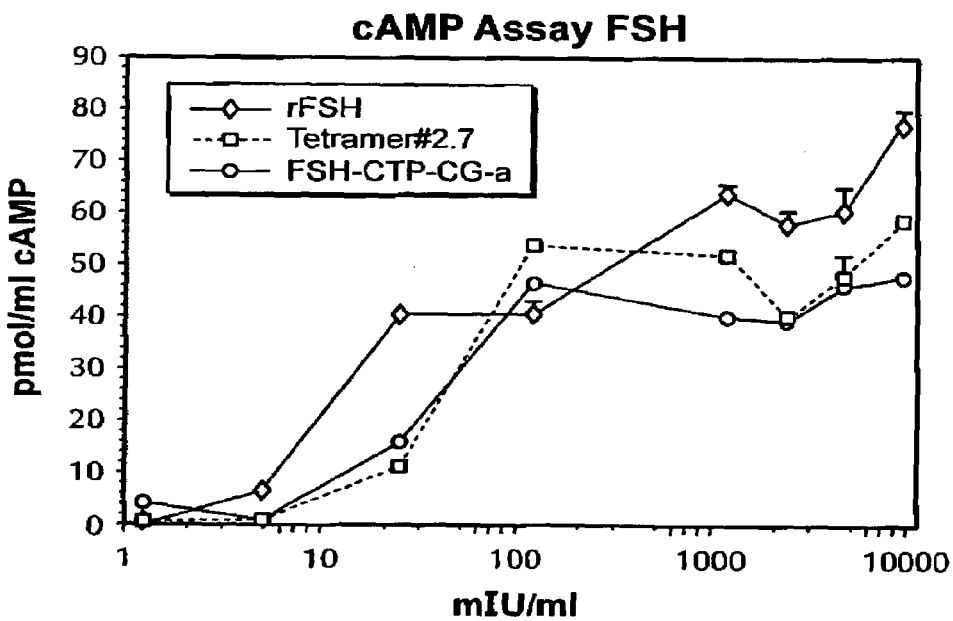
FIG. 5 is a graph showing the ability of the construct shown in FIG. 1 to activate the FSH receptor.
Figure 6:
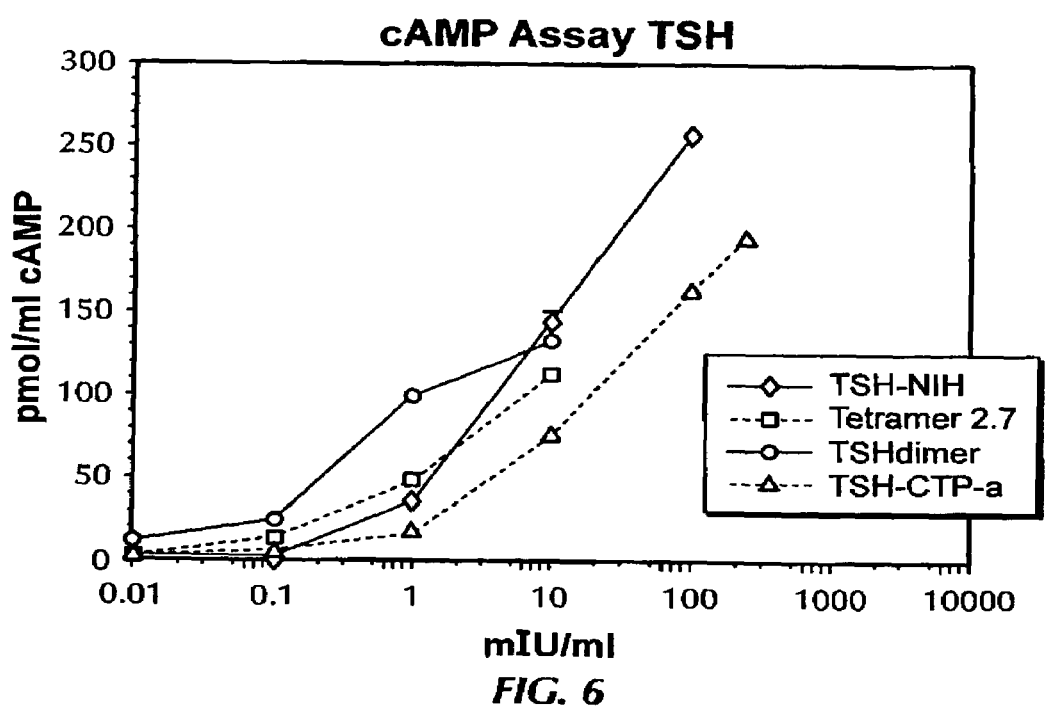
FIG. 6 is a graph showing the ability of the construct shown in FIG. 1 to activate the TSH receptor.

The results for the three β subunit component related receptors are shown in FIGS. 4–6.

FIG. 4 shows the results when the tetramer T.7 was tested in comparison with CG heterodimer. The ability of each to stimulate cAMP production is comparable.

FIG. 5 shows the results when the test is performed with respect to the FSH receptor. The tetramer (solid squares) shows stimulating activity comparable both to recombinant FSH (solid diamonds) and as compared to the single chain FSH-CTP-CG-α (solid circles).

Similar results were obtained with regard to TSH receptor agonist activity. As shown in FIG. 6, tetramer 2.7 (solid squares) is only slightly less agonistic than the TSH dimer (solid circles) or TSH obtained from NIH (solid diamonds); all of these compounds were more effective agonists than the single chain form TSH-CTP-α (open triangles).

What is claimed is:

1. A glycosylated or nonglycosylated proteinaceous compound having agonist activity for at least one glycoprotein hormone, and having a structure selected from the group consisting of $$\beta^1\text{-(linker}^1)_{n^1}\text{-}\beta^2\text{(linker}^2)_{n^2}\text{-}\beta^3\text{-(linker}^3)_{n^3}\text{-}\alpha \tag{1}$$

$$\beta^1\text{-(linker}^1)_{n^1}\text{-}\beta^2\text{-(linker}^2)_{n^2}\text{-}\alpha\text{-(linker}^3)_{n^3}\text{-}\beta^3 \tag{2}$$

$$\beta^1\text{-(linker}^1)_{n^1}\text{-}\alpha\text{-(linker}^2)_{n^2}\text{-}\beta^2\text{-(linker}^3)_{n^3}\text{-}\beta^3 \tag{3}$$

and $$\alpha\text{-(linker}^1)_{n^1}\text{-}\beta^1\text{-(linker}^2)_{n^2}\text{-}\beta^2\text{-(linker}^3)_{n^3}\text{-}\beta^3 \tag{4}$$

wherein α is the α subunit of a vertebrate glycoprotein hormone or a variant thereof that binds to the corresponding glyco protein hormone receptor;

each β is independently a glycoprotein β subunit or a variant thereof;

each "linker" is a hydrophilic, flexible spacer equivalent to a peptide containing 1–100 amino acid residues; and each n is a 0 or 1;

said compound optionally comprising one or more additional $\beta^x\text{(linker}^x)_{n^x}$ and/or one or more additional α glycoprotein hormone subunits.

2. The compound of claim 1 which is of the formula $$\beta^1\text{-(linker}^1)_{n^1}\text{-}\beta^2\text{-(linker}^2)_{n^2}\text{-}\beta^3\text{-(linker}^3)_{n^3}\text{-}\alpha; \tag{1}$$

$$\beta^1\text{-(linker}^1)_{n^1}\text{-}\beta^2\text{-(linker}^2)_{n^2}\text{-}\alpha\text{-(linker}^3)_{n^3}\text{-}\beta^3; \tag{2}$$

$$\beta^1\text{-(linker}^1)_{n^1}\text{-}\alpha\text{-(linker}^2)_{n^2}\text{-}\beta^2\text{-(linker}^3)_{n^3}\text{-}\beta^3; \tag{3}$$

$$\alpha\text{-(linker}^1)_{n^1}\text{-}\beta^1\text{-(linker}^2)_{n^2}\text{-}\beta^2\text{-(linker}^3)_{n^3}\text{-}\beta^3; \tag{4}$$

$$\beta^1(\text{linker}^1)_{n^1}\text{-}\beta^2(\text{linker}^2)_{n^2}\text{-}\beta^3(\text{linker}^3)_{n^3}\text{-}\beta^4(\text{linker}^4)_{n^4}\text{-}\alpha; \tag{5}$$

$$\beta^1(\text{linker}^1)_{n^1}\text{-}\beta^2(\text{linker}^2)_{n^2}\text{-}\beta^3(\text{linker}^3)_{n^3}\text{-}\alpha\text{-}\beta^4(\text{linker}^4)_{n^4}; \tag{6}$$

$$\beta^1(\text{linker}^1)_{n^1}\text{-}\beta^2(\text{linker}^2)_{n^2}\text{-}\alpha\text{-}\beta^3(\text{linker}^3)_{n^3}\text{-}\beta^4(\text{linker}^4)_{n^4}; \tag{7}$$

$$\beta^1(\text{linker}^1)_{n^1}\text{-}\alpha\text{-}\beta^2(\text{linker}^2)_{n^2}\text{-}\beta^3(\text{linker}^3)_{n^3}\text{-}\beta^4(\text{linker}^4)_{n^4}; \text{ or} \tag{8}$$

$$\alpha\text{-}\beta^1(\text{linker}^1)_{n^1}\text{-}\beta^2(\text{linker}^2)_{n^2}\text{-}\beta^3(\text{linker}^3)_{n^3}\text{-}\beta^4(\text{linker}^4)_{n^4}. \tag{9}$$

3. The compound of claim 1 or 2 wherein each β is different.

4. The compound of claim 1 or 2 wherein at least one linker is independently a complete or partial CTP comprising at least one glycosylation site or a variant thereof, wherein CTP refers to the amino acid sequence at positions 112–118 to 145 of human chorionic gonadotropin β subunit.

5. The compound of claim 1 or 2 wherein said protein consists of naturally occurring amino acids.

6. The compound of claim 1 or 2 wherein each β and α subunit is human native subunit.

7. The compound of claim 1 which is of formula (1).

8. The compound of claim 7 which is TSHβ-CTP-FSHβ-CTP-CGβ-α.

9. The compound of claim 2 which is of formula (5).

10. The compound of claim 9 wherein each β subunit is different.

11. The compound of claim 1 or 2 coupled to a solid support.

* * * * *